(12) United States Patent
Kuenstner

(10) Patent No.: US 6,393,310 B1
(45) Date of Patent: May 21, 2002

(54) METHODS AND SYSTEMS FOR CLINICAL ANALYTE DETERMINATION BY VISIBLE AND INFRARED SPECTROSCOPY

(76) Inventor: J. Todd Kuenstner, 26 Wild Duck Rd., Wyckoff, NJ (US) 07481

(*) Notice: Subject to any disclaimer, the term of this patent is extended or adjusted under 35 U.S.C. 154(b) by 0 days.

(21) Appl. No.: 09/391,986

(22) Filed: Sep. 9, 1999

Related U.S. Application Data

(60) Provisional application No. 60/099,568, filed on Sep. 9, 1998.

(51) Int. Cl.[7] .................................................. A61B 5/00
(52) U.S. Cl. ........................ 600/322; 600/310; 600/328
(58) Field of Search ............................... 600/309–310, 600/322–324, 326, 328; 356/39–42

(56) References Cited

U.S. PATENT DOCUMENTS

| | | | |
|---|---|---|---|
| 4,878,021 A | | 10/1989 | Granot ........................ 324/309 |
| 4,915,111 A | | 4/1990 | Sano et al. |
| 4,997,769 A | | 3/1991 | Lundsgaard .................. 436/66 |
| 5,072,732 A | | 12/1991 | Rapoport et al. |
| 5,127,406 A | | 7/1992 | Yamaguchi |
| 5,137,023 A | | 8/1992 | Mendelson et al. |
| 5,178,142 A | | 1/1993 | Harjunmaa et al. |
| 5,183,042 A | | 2/1993 | Harjunmaa et al. |
| 5,204,532 A | | 4/1993 | Rosenthal ................... 250/341 |
| 5,261,405 A | | 11/1993 | Fossel |
| 5,337,745 A | | 8/1994 | Benaron |
| 5,377,674 A | * | 1/1995 | Kuestner ..................... 600/328 |
| 5,448,349 A | | 9/1995 | Kosaka ......................... 356/73 |
| 5,533,509 A | * | 7/1996 | Koashi et al. ................ 600/316 |
| 5,553,616 A | | 9/1996 | Ham et al. |
| 5,692,503 A | * | 12/1997 | Kuenstner ................... 600/322 |
| 5,879,294 A | * | 3/1999 | Anderson et al. ........... 600/310 |
| 6,161,028 A | * | 12/2000 | Braig et al. ................. 600/316 |

OTHER PUBLICATIONS

*"Rapid Measurement of Analytes in Whole Blood with NIR Transmittance," *Leaping Ahead with Near Infrared Spectroscopy,* edited by G.D. Batten, et. al., NIR Spectroscopy Group, Royal Australian Chemical Institute, Victoria, Australia, pp. 431–436, Apr. 1994.
*"Spectrophotometry of Human Hemoglobin in the Near Infrared Region from 1000 to 2500 nm," *Journal of Near Infrared Spectroscopy,* 2, 59–65, 1994.

"Noninvasive Glucose Monitoring in Diabetic Patients: A Preliminary Evaluation," *Clinical Chemistry,* vol. 38, M. Noda, et. Al, No. 9, 1992.
"Pulse Oximetry: Analysis of Theory, Technology and Practice," *J. Clin. Monit.,* vol. 4, pp.290–301, 1988.
"Measurement of Hemoglobin in Unlysed Blood Using Near Infrared Spectroscopy," *Applied Spectroscopy,* 48 (4), 484, 1994.
"Solid–State Matrix Effects on Near–Infrared Spectra: Interactions of Glucose and Sucrose with Amylose, Amylopectin Cellulose, and Starch—Implications for Near–Infared Calibrations," *Applied Spectroscopy,* vol. 50, No. 2, pp. 154–160, 1996.
"Completely Noninvasive Measurements of Human Blood Glucose In Vivo Using Near Infrared Waves," *Pathogenesis and Treatment of NIDDM and its Related Problems,* Elsevier Science, B.V., 1994.
"Near–Infared Spectrometric Determination of Hydrogen Ion, Glucose, and Human Serum Albumin in a Simulated Biological Matrix," *Spectroscopy,* James K. Drennen, et al., vol. 6, No. 2, May 1990.
"More on Derivatives. Part I. Segments, Gaps and 'Ghosts'," *NIR News,* vol. 4, No. 6.

* cited by examiner

Primary Examiner—Eric F. Winakur
Assistant Examiner—Matthew Kremer
(74) *Attorney, Agent, or Firm*—Kilpatrick Stockton LLP

(57) ABSTRACT

Noninvasive, in-vivo, methods and system for determining a person's relative individual percentages of a plurality of hemoglobin species and for determining a person's total hemoglobin concentration, as well as, the concentration of the hemoglobin species which contribute to this total concentration, i.e., oxy-, deoxy-, carboxy-, met- and sufhemoglobin are described. In a first embodiment, analyte wavelengths are selected in the visible region from 510 nm to 620 nm, with separate analyte wavelengths for each hemoglobin species to determine relative individual percentages. The measurements are then combined in a series of simultaneous equations which are then solved for the concentration of each species and the total concentration of hemoglobin. In a second embodiment, wavelengths in the near infrared region from 650 nm to 1000 nm and derivative spectra are employed to determine total hemoglobin concentration, as well as, the concentration of the hemoglobin species which contribute to this total concentration.

9 Claims, No Drawings

METHODS AND SYSTEMS FOR CLINICAL ANALYTE DETERMINATION BY VISIBLE AND INFRARED SPECTROSCOPY

CROSS REFERENCE TO RELATED APPLICATION

This application claims the benefit of U.S. Provisional Application No. 60/099,568 filed Sep. 9, 1998 and entitled "Clinical Analyte Determination by Infrared Spectroscopy."

FIELD OF THE INVENTION

The present invention relates to noninvasive clinical analyte determination by visible and infrared spectrsocopy, and more particularly, to methods and systems for measuring relative individual percentages of a plurality of hemoglobin species including oxy-, deoxy-, carboxy- and met- hemoglobin ($HbO_2$, Hb, HbCO and Hi, respectively) and for measuring hemoglobin species concentrations including, oxyhemoglobin, deoxyhemoglobin, carboxyhemoglobin, methemoglobin and sulfhemoglobin (HbS). These methods and systems may also be applied invasively or to whole blood samples.

BACKGROUND

The measurement of the levels of blood borne analytes, such as hemoglobin species and total hemoglobin concentration in a patient, is an often utilized clinical procedure. Typically, a needle or some other device is used to deeply penetrate a patient's skin and draw a sample, such as blood, which is then analyzed by chemical techniques to determine the concentration of the analyte(s) of interest. The drawbacks of these procedures include the pain and apprehension experienced by the patient, the risk of infection to both the patient and any health care worker handling the sample or the sample-taking device, and the delay in feedback associated with sending the sample to a laboratory for analysis.

The use of absorbance data at multiple wavelengths combined in ratio form and the use of derivative absorbance ratios for noninvasive measurements of hemoglobin was first described in my U.S. Pat. No. 5,377,674, the disclosures of which is hereby incorporated by reference. As set forth in U.S. Pat. No. 5,377,674, hemoglobin concentration may be accurately measured noninvasively (in-vivo), as well as invasively or in whole blood (in-vitro), using many regions of the visible and near-infrared spectrum and many different data treatments. The data treatments which were presented included derivative data treatments which do not require a path-length or scattering measurement and therefore could be readily used with a device modeled on the pulse oximeter to obtain measurements at the peak and trough of blood pulsation. The use of absorbance data at multiple wavelengths combined in ratio form and the use of derivative absorbance ratios for noninvasive measurements of hemoglobin was first described in U.S. Pat. No. 5,377,674.

Spectroscopy deals with the measurement and interpretation of light waves resulting from exposing a substance to a known light wave. The measurements can be based on the reflectance, transmission or emission of the light wave. When exposing a mixture of substances to a known light wave, each of the substances absorbs, to varying degrees, parts of the light wave. As a result of this absorption, a unique light wave is created. Thus, the unique resultant light wave can be measured and interpreted to determine the presence and concentration of substances that comprise the mixture. I have shown in prior work that spectral regions may be normalized prior to PLS analysis by dividing by the area of the absolute value of the derivative spectrum to yield analyte concentration information. (Kuenstner et. al., "Rapid Measurement of Analytes in Whole Blood with NfR Transmittance," *Leaping Ahead With Near Infrared Spectroscopy*, edited by G. Batten et. al., Proceedings of the 6th International Conference on Near Infrared Spectroscopy at Lorne, Australia in April 1994).

Transmittance, reflectance and emission techniques have been developed for measuring analytes in samples. In general, however, these methods have been found to be accurate for some, but not all, patients. To improve the accuracy, the prior art typically requires the use of complex analysis, complex equipment, or both. Thus, these methods are not well-suited for convenient, quick and simple use.

Additionally, to overcome the delay in feedback associated with sending the sample to a laboratory for analysis, the use of point of care testing has increased. Generally, this type of testing means that patient samples are tested at the bedside or within the intensive care unit of the hospital ward rather than in a centralized laboratory. Many of the present point of care methods, however, are more expensive than the conventional methods. For example, one widely-used point of care device, made by the I-Stat Corporation of Princeton, N.J., analyzes whole blood for sodium, potassium, chloride, $CO_2$, urea, glucose and hematocrit. The cost of reagents for this panel of tests is about twelve dollars. In contrast, the reagent cost per analyte for a typical large central laboratory analyzer is approximately a few cents. Thus, the benefit and practicality of current devices providing immediate feedback may be outweighed by the cost, especially given the fiscal constraints of today's hospital environment.

Another point of care device is the pulse oximeter. Current pulse oximeters, however, measure $HbO_2$ and Hb, and are subject to inaccuracy when there are significant quantities of HbCO and Hi.

Further details and background relating to hemoglobin species concentration measurement may be found in my U.S. Pat. No. 5,692,503, the disclosure of which is also incorporated herein by reference.

SUMMARY OF THE INVENTION

The present invention provides methods and systems for evaluating hemoglobin in a patient. The methods and systems of the present invention may be utilized to measure relative individual percentages of a plurality of hemoglobin species in tissue including oxy-, deoxy-, carboxy- and met-hemoglobin ($HbO_2$, Hb, HbCO and Hi, respectively) and to measure total hemoglobin concentration in tissue and/or the concentration of individual hemoglobin species including, oxyhemoglobin, deoxyhemoglobin, carboxyhemoglobin, methemoglobin and sulfhemoglobin (HbS).

According to the methods and systems of the present invention, the relative percentages of a plurality of hemoglobin species and the concentration measurements of hemoglobin species are obtained through the use of spectrophotometric measurements in the visible and/or the short-wavelength near infrared regions. The advantages of using this part of the electromagnetic spectrum include: that light sources, such as LED's, suitable for use in hand-held instruments for the spectrophotometric measurements are currently available; and the possibility of measuring the various species of hemoglobin in addition to the total hemoglobin concentration. The spectrophotometric measurements are described with reference to absorbance, however the methods and systems of the present invention may also utilize other spectrophotometric measurements such as transmission, reflectance or emission.

In a first aspect, methods and systems of the present invention utilize spectrophotometric measurements in the visible region from 510 nanometers (nm) to 620 nm. The resulting spectrophotometric data is normalized by dividing by a difference of spectrophotometric data at two other wavelengths and is entered in a series of four simultaneous equations with four unknowns (the concentrations of $HbO_2$, Hb, HbCO and Hi) which can then be solved for each unknown by applying matrix algebra. Insight into the nature of the absorbance spectra of the hemoglobin species shows that one favorable difference term is the absorbance at 510 nm minus the absorbance at 620 nm. At 510 nm and at 620 nm, the absorptivity of all four species is similar but not equal and the difference in absorptivity for each type of hemoglobin between these two points is similar. A difference of absorbance at 510 nm and at 620 nm should not vary greatly regardless of the concentration of the various hemoglobin species in any mixture.

In a second aspect, the methods and systems of the present invention may utilize spectrophotometric measurements in the near-infrared region. Detailed spectroscopic measurements of whole arterial blood in the region from 650 nm to 1000 nm would be obtained. This information is analyzed in order to find the best region or regions for measuring the various hemoglobin species. The spectra would be normalized by dividing by the area of the absolute value of the first or second derivative spectrum in the region of interest. Next, the spectra would be mean centered and then analyzed with a partial least squares (PLS) or artificial neural networks (ANN) program. This approach is expected to yield measurements which are at least comparable in accuracy to those reported in the in-vitro oximetry literature.

The systems of the present invention comprise apparatus for performing the methods of the present invention. According to the second aspect of the present invention, a system for measuring hemoglobin species comprises a broad-band light source and a diode array detector. The broad-band light source provides light at the wavelengths described above with reference to the methods of the present invention. The diode array detector is utilized to take the spectrophotometric measurements. This approach is unique since it would allow for obtaining a partial spectrum rather than information from several discrete light sources. The broad-band light source and the diode array detector may be placed side by side with an intervening shield so that the light which strikes the detector is reflected light rather than transmitted light.

Alternatively, a system of the present invention may be utilized to acquire spectrophotometric measurements through a thin piece of tissue since this tissue is relatively transparent to light in this region of the spectrum. The diode array detector permits a simultaneous measurement at a multiplicity of wavelengths thereby yielding a spectrum. Spectra are sampled over time so that subtraction of one spectrum from a subsequent spectrum would yield a spectrum which is due to arterial blood alone. Many such arterial blood spectra would be averaged and then these spectra could be analyzed using PLS or ANN in a correlation study with the standard in-vitro oximetry method. One possible embodiment may include a diode array detector which detects wavelengths from 650 nm to 1000 nm.

As will be understood from the foregoing description, the methods and systems of the present invention provide numerous advantages for measuring and determining relative percentages of and/or concentration of individual hemoglobin species.

The methods and systems of the present invention may advantageously be utilized in a noninvasive (in-vivo) fashion to provide point of care determination of relative individual percentages of hemoglobin concentration and/or hemoglobin species concentration.

The methods and systems of the present invention may also be advantageously utilized in a laboratory setting to rapidly and accurately determine relative individual percentages of hemoglobin concentration and of hemoglobin species concentration invasively or in blood samples (in-vitro).

Further features and advantages of the present invention will become apparent from the following more detailed description.

DETAILED DESCRIPTION OF THE INVENTION

A method of the present invention for determining the relative percentages of a plurality of hemoglobin species comprises:

generating a spectrophotometric measurement by measuring a spectrophotometric property of light at a plurality of wavelengths in capillary bed tissue said plurality of wavelengths including:
  at least one analyte wavelength for a first hemoglobin species;
  at least one analyte wavelength for at least a second hemoglobin species;
  a first reference wavelength; and
  a second reference wavelength;
calculating the difference in the spectrophotometric property at the first reference wavelength and the second reference wavelength to define a difference term;
normalizing the spectrophotometric measurement at each analyte wavelength utilizing the ratio of the spectrophotometric measurement at the analyte wavelength to the difference term; and
determining relative percentages of the hemoglobin species. The determination of the relative percentages may be performed utilizing conventional matrix algebra techniques after normalization of the measurements.

The plurality of wavelengths may further comprise at least one analyte wavelength for additional and/or all hemoglobin species wherein the spectrophotometric measurement for each additional analyte wavelength is normalized utilizing the difference term and the normalized measurement is utilized to determine the relative percentage of each hemoglobin species. Preferably, the plurality of wavelengths, analyte and reference, comprise wavelengths from 510 nm to 620 nm. The reference wavelengths may be the same or different as the analyte wavelengths.

The methods of the present invention may further comprise:

isolating the spectrophotometric measurement due to arterial blood by
generating a peak spectrophotometric measurement by measuring a spectrophotometric property at the plurality of wavelengths during the peak of blood pulsation through the tissue;
generating a trough spectrophotometric measurement by measuring a spectrophotometric property at the plurality of wavelengths during the trough of blood pulsation through the tissue; and
subtracting the trough spectrophotometric measurement from the peak spectrophotometric measurement to isolate the spectrophotometric measurement due to arterial blood.

In order to ensure the accuracy of the method, the method may be performed on a sample having known percentages of hemoglobin species as described in Example I below.

A preferred spectrophotometric measurement is an absorbance measurement. As will be understood by those of ordinary skill in the art from the discussion contained herein, the methods of the present invention may also utilize other spectrophotometric measurements, such as transmittance, reflectance, or emittance.

The method of the present invention may be utilized to measure the relative individual percentages of a plurality of known hemoglobin species including oxyhemoglobin, deoxyhemoglobin, carboxyhemoglobin, methemoglobin, and sulfhemoglobin. The method may be utilized with methods for hemoglobin concentration measurement, such as the method described below, in order to determine the relative concentration of each hemoglobin species to total hemoglobin concentration.

The methods of the present invention may be utilized in vivo or in vitro. The methods described herein are generally described with reference to an in vivo embodiment wherein a spectrophotometric measurement is obtained in a noninvasive, or minimally invasive, fashion from capillary bed tissue, for example tissue at a patient's finger or ear. The methods may also be utilized in vitro by generating a spectrophotometric measurement from a blood sample.

In a first embodiment of a method of the present invention, the concentration of known hemoglobin species including oxyhemoglobin, deoxyhemoglobin, carboxyhemoglobin, and methemoglobin may be determined through the solution of a set of N equations with N unknowns where each unknown is a concentration of a particular hemoglobin species. The total number of hemoglobin species whose concentration is to be determined equals N.

The first equation in the set of N equations is generated by: measuring the absorbance of light at a plurality of wavelengths including a first analyte wavelength; a first reference wavelength; and a second reference wavelength. The second equation in the set of N equations is generated by measuring the absorbance of light at a plurality of wavelengths including a second analyte wavelength and the first and second reference wavelengths. The third equation in the set of N equations is generated by measuring the absorbance of light at a plurality of wavelengths including a third analyte wavelength and the first and second reference wavelengths. Additional equations in the set of N equations may be generated in the same fashion.

The preferred wavelengths to utilize for the first, second, third, fourth, etc. analyte wavelengths include those in the visible region between 510 nm to 620 nm. This same region of the spectrum is used by the current in-vitro oximeters. Most investigators regard this region as inaccessible in tissue because of the intense absorption of light by tissue at these wavelengths. While there certainly is intense absorption of light by tissue in this region, reflectance spectra of the human hand in this part of the spectrum suggest that a reflectance measurement could sample sufficient tissue for in-vivo measurements.

The proposed method, which may be utilized in-vivo, could share some features of the measurements made by the in-vitro oximeters. These instruments lyse whole blood, use a fixed path-length and make measurements at at least four wavelengths. The resulting data can be entered in a series of four simultaneous equations with four unknowns (the concentrations of $HbO_2$, Hb, HbCO and Hi) which can then be solved for each unknown. The proposed in-vivo method will use the above approach except that the equations will be modified so that knowledge of the path-length is unnecessary. In the in-vivo setting, the path-length is generally not an easily measured quantity.

One way to eliminate the pathlength is to divide the absorbance by a difference of absorbance at two other wavelengths. These wavelengths may be referred to as "reference wavelengths". Other approaches are probably possible, as well, and an alternative approach is presented later in this application. Insight into the nature of the absorbance spectra of the hemoglobin species along with trial and error calculation show that one favorable difference term is the absorbance at 510 nm minus the absorbance at 620 nm. At 510 nm and at 620 nm, the absorptivity of all four species is similar but not equal and the difference in absorptivity for each type of hemoglobin between these two points is similar. In a mixture of hemoglobins, a difference of absorbance at 510 nm and at 620 nm should not vary greatly regardless of the concentration of the various hemoglobin species in any mixture.

This principle may be demonstrated in the following way. Table 1 shows the absorptivities of the different types of hemoglobin at the 510 nm, 555 nm, 569 nm, 577 nm and at 620 nm. The absorptivities at 510 nm, at 555 nm, 569 nm and at 577 nm represent local maxima for met-, deoxy-, carboxy- and oxyhemoglobin, respectively. The absorptivities at 510 nm and at 620 nm may be used to form a difference term. The values denoted by an asterisk are extrapolated values obtained from spectra of pure hemoglobin species while all of the other values are from a textbook by Onno Van Assendelft.

TABLE 1

Absorptivity Data For Pure Hemoglobin Species

|        | $HbO_2$ | Hb    | HbCO   | Hi    |
|--------|---------|-------|--------|-------|
| 510 nm | 4.76    | 5.33  | 5.84*  | 8.99* |
| 555 nm | 9.28*   | 13.04 | 11.33  | 4.75* |
| 569 nm | 11.27   | 11.27 | 14.31  | 4.14* |
| 577 nm | 15.37   | 9.25* | 10.30* | 4.16* |
| 620 nm | 0.23    | 1.23  | 0.33   | 3.41* |

The proposed method of measurement will use a difference term of the absorbance at 510 nm minus the absorbance at 620 nm as a divisor to be used to eliminate pathlength considerations from the calculations. Using the absorptivity data from the above table, it can be shown that the difference in absorptivity between 510 nm and 620 nm is quite similar for each of the hemoglobin species.

| $HbO_2$ | $a_{510} - a_{620} = 4.76 - .23 = 4.53$ |
| Hb      | $a_{510} - a_{620} = 5.33 - 1.23 = 4.1$ |
| HbCO    | $a_{510} - a_{620} = 5.84 - .33 = 5.51$ |
| Hi      | $a_{510} - a_{620} = 8.99 - 3.41 = 5.58$ |

On the other hand, one could examine how much this difference term comprising absorbance at 510 nm minus the absorbance at 620 nm, will vary when the composition of a solution of hemoglobin species is varied. This method of measurement may be tested in an ideal setting consisting of mixtures of spectra of pure hemoglobin species. The spectra of the hemoglobin species were obtained using a Hewlett Packard ultra violet visible spectrometer with very short pathlength cuvettes made by the Avoximeter Corporation of San Antonio, Tex. The mixtures of spectra were obtained using the Galactic software program for spectroscopy. It should be noted that each of the spectra of pure hemoglobin species used the same pathlength and thus the pathlength was the same in all of these examples. A mixture of 90% $HbO_2$ and 10% Hb will be denoted by OXDE90, a mixture of 75% $HbO_2$ and 25% Hb will be denoted by OXDE75, a mixture of 50% $HbO_2$ and 50% Hb will be denoted by OXDE50, a mixture of 50% $HbO_2$ and 50% Hi will be denoted by OXME50, a mixture of and 80% $HbO_2$ and 20% HbCO will be denoted by OXCO80 and a mixture of 50% $HbO_2$ and 50% HbCO will be denoted by OXCO50. The absorbances at selected points for these mixtures of hemoglobin species are listed below in Table 2.

TABLE 2

Absorbances Of The Various Mixtures Of Hemoglobin Species

|  | OXDE90 | OXDE75 | OXDE50 | OXME50 | OXCO80 | OXCO50 |
|---|---|---|---|---|---|---|
| 510 nm | .482 | .489 | .500 | .637 | .497 | .526 |
| 555 nm | .910 | .951 | 1.018 | .652 | .919 | .973 |
| 569 nm | 1.049 | 1.044 | 1.036 | .715 | 1.106 | 1.188 |
| 577 nm | 1.347 | 1.271 | 1.144 | .890 | 1.3070 | 1.171 |
| 620 nm | .073 | .090 | .117 | .208 | 0.65 | .068 |

The mixtures of hemoglobin species shown above in Table 2 vary greatly in composition. However, as shown in the calculations shown below, large variations in the composition of these mixtures only result in small variations in the difference term. This relatively small variation in the difference term implies that this term would be insensitive to changes in composition of the mixtures of hemoglobin and thus would also be a good divisor term to be used for removing pathlength considerations.

| OXDE90 | $A_{510}-A_{620} = .482 - .073 = .409$ |
| OXDE75 | $A_{510}-A_{620} = .489 - .090 = .399$ |
| OXDE50 | $A_{510}-A_{620} = .500 - .117 = .383$ |
| OXCO80 | $A_{510}-A_{620} = .497 - .065 = .432$ |
| OXCO50 | $A_{510}-A_{620} = .526 - .068 = .458$ |
| OXME50 | $A_{510}-A_{620} = .637 - .208 = .429$ |

The following discussion will describe how measurements of the quantities of the various hemoglobin species may be made in any mixture of hemoglobin species without knowledge of the pathlength of the system. Beer's Law may be applied to mixtures of different substances so long as they act independently. Under these circumstances, the absorbances due to each substance are additive and since each substance will have its own absorptivity, and the law may be written for a given wavelength as $$A_{tot} = a_1 b c_1 + a_2 b c_2 + \ldots$$

In the case of a mixture of hemoglobin species in blood in which it is assumed that for the region of 510 nm to 620 nm, there are no other significant substances absorbing light, the above expression becomes $$A_{tot} = a_{HbO2} b c_{HbO2} + a_{Hb} b c_{Hb} + a_{HbCO} b c_{HbCO} + a_{Hi} b c_{Hi}$$

A system of four such equations at four different wavelengths can be solved for the four unknown concentrations, $c_{HbO2}$, $c_{Hb}$, $c_{HbCO}$ and $c_{Hi}$. However, before examples are shown in which the concentrations of the four hemoglobin species may be solved for unknown mixtures, the method for removing pathlength from these equations will be described. The pathlength may be removed by dividing by a difference term of $A_{510}-A_{620}$. Using the Beer's Law equation at 510 nm and using more abbreviated notation for $HbO_2$, Hb, HbCO and Hi which are respectively, O, D, C and M $$A_{510}(A_{510}-A_{620})^{-1} = (a_{O510}bc_O + a_{D510}bc_D + a_{C510}bc_C + a_{M510}bc_M) \times$$
$$((a_{O510}bc_O + a_{D510}bc_D + a_{C510}bc_C + a_{M510}bc_M) - (a_{O620}bc_O + a_{D620}bc_D + a_{C620}bc_C + a_{M620}bc_M))^{-1}$$

In the above equations, b divides out and since $(c_O + c_D + c_C + c_M) = C_{totHgb}$ and as shown earlier, $(a_{O510} - a_{O620}) = (a_{D510} - a_{D620}) = (a_{C510} - a_{C620}) = (a_{M510} - a_{M620})$, so the above equation becomes $$A_{510}(A_{510}-A_{620})^{-1} = a_{O510}(a_{O510}-a_{O620})^{-1} c_O/c_{tot} + a_{D510}$$
$$(a_{D510}-a_{D620})^{-1} c_D/c_{tot} + a_{C510}(a_{C510}-a_{C620})^{-1} c_C/c_{tot} + a_{M510}$$
$$(a_{M510}-a_{M620})^{-1} c_M/c_M/c_{tot}$$

Using absorbance data for the various mixtures of hemoglobin species listed in Table 2, the equations of the form shown above and at four different wavelengths may be solved for the concentrations of $HbO_2$, Hb, HbCO and Hi. A system of four simultaneous equations with four unknowns may easily be solved using the Mathcad 7 Professional software program made by MathSoft, Inc., Cambridge, Mass.

Example 1 provides an example of a method of the present invention utilizing measurements in the visible light region.

In another aspect, the present invention provides a method for determining the concentration of a hemoglobin species comprising:

generating an spectrophotometric measurement by measuring a spectrophotometric property of light at a plurality of wavelengths in capillary bed tissue said plurality of wavelengths including:
at least one analyte wavelength for a hemoglobin species;
at least one derivative spectrum for the hemoglobin species;
utilizing a ratio of the spectrophotometric measurement at an analyte wavelength to the derivative spectrum to generate the spectrophotometric measurement; and
comparing the spectrophotometric measurement to a reference curve generated by a correlation study to determine the concentration of the hemoglobin species, wherein the plurality of wavelengths comprise wavelengths from 650 to 1000 nm.

The methods of the present invention utilize reference data to correlate the absorbance data obtained from the capillary bed tissue (in-vivo), or blood sample (in-vitro) to the concentration of the analyte being measured. Generation of suitable reference data is well within the skill of those of ordinary skill in the art. In general, reference data may be gathered, and a reference curve, or the like, generated by performing the method of the present invention on blood samples having known concentrations of the analyte to be measured. The data obtained by the method of the present invention may then be directly correlated to a known concentration of the analyte to generate a reference curve for future use. In the in-vivo embodiment, a reference curve is preferably generated by comparing and correlating the data obtained by the method of the present invention to the concentration of the analyte obtained by a traditional invasive method to generate a reference curve. Preferably, the reference data and correlation data are stored electronically in the device utilized to generate the absorbance data and the absorbance data is immediately and directly compared to the reference data to provide the concentration of the analyte or analytes.

In this embodiment, detailed spectroscopic measurements of whole arterial blood in the region from 650 nm to 1000 nm are obtained. This information is then analyzed in order to find the best region or regions for measuring the various hemoglobin species. The spectra would be normalized by dividing by the area of the absolute value of the first or second derivative spectrum in the region of interest. Next, the spectra would be mean centered and then analyzed with a partial least squares (PLS) or artificial neural networks (ANN) program. This approach is expected to yield measurements which are at least comparable in accuracy to those reported in the in-vitro oximetry literature.

Having found the region or regions which are best for measuring the various hemoglobin species, a device could be constructed utilizing a broad-band light source in conjunction with a diode array detector. This approach is unique since it would allow for obtaining a partial spectrum rather than information from several discrete light sources. The light and detector would be placed side by side with an intervening shield so that the light which strikes the detector is reflected light rather than transmitted light.

Alternatively, spectrphotometric measurements could be made through a thin piece of tissue since this tissue is relatively transparent to light in this region of the spectrum. The diode array detector would permit a simultaneous measurement at a multiplicity of wavelengths thereby yielding a spectrum. Spectra would be sampled over time so that subtraction of one spectrum from a subsequent spectrum would yield a spectrum which is due to arterial blood alone. Many such arterial blood spectra would be averaged and then these spectra could be analyzed using PLS or ANN in a correlation study with the standard in-vitro oximetry method. One possible embodiment may include a diode array detector which detects wavelengths from 650 nm to 1000 nm.

Further details of this embodiment are illustrated in Example 2.

EXAMPLE 1

This example illustrates the use of the visible light region to measure relative individual percentages of a plurality of hemoglobin species.

For the mixture of hemoglobin species denoted by OXDE50, using data from Tables 1 and 2, the series of four simultaneous equations with four unknowns is shown below.

at 510 nm $$0.5(0.5-0.117)^{-1} = 4.76(4.76-0.23)^{-1}O + 5.33(5.33-1.23)^{-1}D + 5.84(5.84-0.33)^{-1}C + 8.99(8.99-3.41)^{-1}M$$

at 555 nm $$1.018(0.5-0.117)^{-1} = 9.28(4.76-0.23)^{-1}O + 13.04(5.33-1.23)^{-1}D + 11.33(5.84-0.33)^{-1}C + 4.75(8.99-3.41)^{-1}M$$

at 569 nm $$1.036(0.5-0.117)^{-1} = 11.27(4.76-0.23)^{-1}O + 11.27(5.33-1.23)^{-1}D + 14.31(5.84-0.33)^{-1}C + 4.14)8.99-3.41)^{-1}M$$

at 577 nm $$1.144(0.5-0.117)^{-1} = 15.37(4.76-0.23)^{-1}O + 9.25(5.33-1.23)^{-1}D + 10.30)5.84-0.33)^{-1}C + 4.16(8.99-3.41)^{-1}M$$

Solving the above set of four simultaneous equations, the predicted composition of the mixture is 56% O and 46%D. The actual composition is 50% O and 50% D. If one normalized the above predictions so that the sum is 100%, the predicted values would be 55% O and 45% D. This predicted composition is quite close to the actual composition.

For the remaining mixtures, the predicted composition, the normalized predicted composition and the actual composition appear in Table 3.

TABLE 3

|  | predicted composition | normalized predicted composition | actual composition |
| --- | --- | --- | --- |
| OXDE90 | 88% O, 11% D | 89% O, 11% D | 90% O, 10% D |
| OXDE75 | 77% O, 23% D | 77% O, 23% D | 75% O, 25% D |
| OXCO80 | 79% O, 18% C | 81% O, 19% C | 80% O, 20% C |
| OXCO50 | 43% O, 55% C | 44% O, 56% C | 50% O, 50% C |
| OXME50 | 46% O, 60% M | 43% O, 57% M | 50% O, 50% M |

While these results are not perfect, they are accurate enough to be clinically useful in an emergency situation and clearly better than the results available from the current pulse oximeter which cannot detect the presence of dyshemoglobins. This method of measurement is probably applicable to other systems as well.

If one were to remove the pathlength from the calculations by dividing by the absorbance at 522 nm rather than dividing by a difference term of absorbance at 510 nm−absorbance at 620 nm, the results of the calculations are shown in Table 4. Note that the absorbance at 522 nm is an isosbestic point for $HbO_2$, Hb, and Hi and a near isosbestic point for HbCO.

TABLE 4

|  | predicted composition | normalized predicted composition | actual composition |
| --- | --- | --- | --- |
| OXDE90 | 80% O, 12% D | 93% O, 7% D | 90% O, 10% D |
| OXDE75 | 68% O, 22% D | 76% O, 24% D | 75% O, 25% D |
| OXDE50 | 48% O, 42% D | 53% O, 47% D | 50% O, 50% D |
| OXCO80 | 66% O, 23% C | 74% O, 26% C | 80% O, 20% C |
| OXCO50 | 37% O, 54% C | 41% O, 59% C | 50% O, 50% C |
| OXME50 | 43% O, 55% M | 44% O, 56% M | 50% O, 50% M |

These results are not quite as good as those which appear in Table 3, however, they are once again probably clinically useful.

EXAMPLE 2

This example illustrates the use of the method of the present invention utilizing spectrophotometric measurements in the near-infrared region.

The foregoing approach using the near-infrared region may be validated by an experimental study using a commercially available spectrophotometer, such as an NIRSystems spectrophotometer. The spectral region to be studied would include 650 nm to 1000 nm. The samples would consist of arterial blood samples with various concentrations of the hemoglobin species which would be determined using an in-vitro oximeter. In order to obtain some of the desired mixtures, some of the samples could be manipulated by the addition of sodium dithionite, carbon monoxide and/or potassium ferricyanide which would result in the production of deoxy-, carboxy- ,met-, and sulf-hemoglobin, respectively. The spectra would be obtained through teflon tubing which would allow easy aspiration and anoxic conditions. These spectra could then be analyzed using normalization of path length by dividing by the area of the absolute value of the derivative spectrum followed by application of PLS or ANN. This set of spectra could then be used for prediction of spectra obtained in the in-vivo setting.

As will be realized by those of ordinary skill in the art from the foregoing description, the methods and system of the present invention presents a simple procedure for in-vivo determination of the relative individual percentages of a plurality of hemoglobin species and determination of the concentration of the various hemoglobin species in the blood.

It should be clearly understood that the forms of the present invention herein described are illustrative only and are not intended to limit the scope of the invention.

I claim:

1. A method for the in-vivo determination of the relative individual percentages of a plurality of hemoglobin species comprising:

generating a spectrophotometric data measurement by measuring a spectrophotometric property of light at a plurality of wavelengths in capillary bed tissue said plurality of wavelengths ranging from 510 to 620 nm and including:
at least one analyte wavelength for a hemoglobin species;
at least one analyte wavelength for at least a second hemoglobin species;
a first reference wavelength; and
a second reference wavelength;

calculating the difference in the spectrophotometric property at the first reference wavelength and the second reference wavelength to define a difference term;

normalizing the spectrophotometric measurement at each analyte wavelength utilizing the ratio of the spectrophotometric measurement at the analyte wavelength to the difference term; and determining relative percentages of the hemoglobin species.

2. The method of claim 1 wherein the hemoglobin species is selected from the group consisting of: oxyhemoglobin, deoxyhemoglobin, carboxyhemoglobin, and methehemoglobin.

3. The method of claim 2 wherein the plurality of analyte wavelengths comprises an analyte wavelength for each of oxyhemoglobin, deoxyhemoglobin, carboxyhemoglobin, and methemoglobin.

4. The method of claim 1 wherein a spectrophotometric data measurement is generated at a plurality, n, of analyte wavelengths corresponding to a plurality, n, of hemoglobin species to be measured and the determination of relative percentages includes a multivariate analysis including the solution of n equations having n variables.

5. The method of claim 4 wherein the plurality of analyte wavelengths comprises an analyte wavelength for each of oxyhemoglobin, deoxyhemoglobin, carboxyhemoglobin, methemoglobin, and sulfhemoglobin.

6. The method of claim 1 wherein the spectrophotometric property is absorbance.

7. The method of claim 1 wherein the spectrophotometric property is reflectance.

8. The method of claim 1 wherein the spectrophotometric property is emission.

9. The method of claim 1 further comprising:

isolating the spectrophotometric measurement due to arterial blood by:

generating a peak spectrophotometric measurement by measuring the absorbance of light at said plurality of wavelengths in capillary bed tissue during the peak of a blood pulsation through the tissue, generating a trough spectrophotometric measurement by measuring the absorbance of the light at said plurality of wavelengths in capillary bed tissue during the trough of a blood pulsation through the tissue;

subtracting the trough spectrophotometric measurement from the peak spectrophotometric measurement to isolate the spectrophotometric measurement due to arterial blood.

* * * * *